United States Patent
Han et al.

(10) Patent No.: US 11,464,953 B2
(45) Date of Patent: Oct. 11, 2022

(54) WATER-SOLUBLE MICRONEEDLE SPICULES AND NON-AQUEOUS COSMETIC COMPOSITION CONTAINING THE SAME

(71) Applicant: PAEAN AESTHETICS INC., Yuseong-gu Daejeon (KR)

(72) Inventors: Kyuboem Han, Yuseong-gu Daejeon (KR); Jongcheon Ha, Yuseong-gu Daejeon (KR)

(73) Assignee: PAEAN AESTHETICS INC., Yuseong-gu Daejeon (KR)

( * ) Notice: Subject to any disclaimer, the term of this patent is extended or adjusted under 35 U.S.C. 154(b) by 50 days.

(21) Appl. No.: 15/778,418

(22) PCT Filed: Nov. 24, 2016

(86) PCT No.: PCT/KR2016/013634
§ 371 (c)(1),
(2) Date: May 23, 2018

(87) PCT Pub. No.: WO2017/091010
PCT Pub. Date: Jun. 1, 2017

(65) Prior Publication Data
US 2018/0344997 A1   Dec. 6, 2018

(30) Foreign Application Priority Data

Nov. 25, 2015 (KR) .................. 10-2015-0165847
Nov. 24, 2016 (KR) .................. 10-2016-0157312

(51) Int. Cl.
*A61M 37/00* (2006.01)
*A61K 9/00* (2006.01)
*A61K 9/06* (2006.01)

(52) U.S. Cl.
CPC ....... *A61M 37/0015* (2013.01); *A61K 9/0021* (2013.01); *A61K 9/06* (2013.01); *A61M 2037/0023* (2013.01); *A61M 2037/0046* (2013.01); *A61M 2037/0053* (2013.01)

(58) Field of Classification Search
None
See application file for complete search history.

(56) References Cited

U.S. PATENT DOCUMENTS

| 5,697,901 A | 12/1997 | Eriksson |
| 6,162,447 A | 12/2000 | Fankhauser et al. |
| 6,290,991 B1 | 9/2001 | Roser et al. |
| 6,351,433 B1 | 2/2002 | Kosugi |
| 2003/0045837 A1 | 3/2003 | Delmore et al. |
| 2006/0202385 A1* | 9/2006 | Xu ............... A61M 37/0015 264/219 |
| 2008/0112886 A1* | 5/2008 | Mitragotri ........... A61K 9/0097 424/9.1 |
| 2010/0228203 A1* | 9/2010 | Quan .............. A61M 37/0015 604/272 |
| 2012/0265145 A1 | 10/2012 | Mefti et al. |
| 2014/0357544 A1 | 12/2014 | Gonzales et al. |
| 2015/0352345 A1* | 12/2015 | Sul .................. A61M 37/0015 604/46 |
| 2018/0303739 A1 | 10/2018 | Han et al. |

FOREIGN PATENT DOCUMENTS

| JP | 2008-284318 A | 11/2008 | |
| KR | 1001638340000 B1 | 12/1998 | |
| KR | 10-0883565 B1 | 2/2009 | |
| KR | 10-2010-0098298 | 9/2010 | |
| KR | 10-2010-0134237 A | 12/2010 | |
| KR | 101206985 B1 * | 11/2012 | |
| KR | 10-2012-0138180 A | 12/2012 | |
| KR | 20140051648 A * | 5/2014 | ........... A61K 9/0021 |
| KR | 10-2014-0009471 A | 7/2014 | |
| KR | 10-2015-0066829 A | 6/2015 | |
| WO | WO-2011015650 A2 * | 2/2011 | .......... B81C 1/00111 |

OTHER PUBLICATIONS

KR20140051648A Translation, accessed from: https://patents.google.com/patent/KR20140051648A/en?oq=KR20140051648, accessed on Jun. 10, 2019, pp. 1-5 (Year: 2019).*
KR101206985B1 Translation, accessed from: https://patents.google.com/patent/KR101206985B1/en?oq=KR101206985, accessed on Jun. 10, 2019, pp. 1-9 (Year: 2019).*
Lee, J.W., et al., "Dissolving Microneedles for Transdermal Drug Delivery", Biomaterials, pp. 2113-2124 (Year: 2008).*
International Search Report and Written Opinion for PCT/KR2014/000603 dated May 27, 2014.
International Search Report and Written Opinion for PCT/KR2016/011468 dated Feb. 17, 2017.

* cited by examiner

*Primary Examiner* — Michael G. Hartley
*Assistant Examiner* — Lance W Rider
(74) *Attorney, Agent, or Firm* — Maier & Maier, PLLC

(57) ABSTRACT

Disclosed herein are water-soluble microneedle spicules for scrubs and a non-aqueous cosmetic composition containing the same. More specifically, the present invention relates to water-soluble microneedle spicules for scrubs, which are in the shape of a triangular pyramid or sexangular pyramid and characterized in that at least any one among the interior angles of the pyramid base of the spicules for scrubs is 90 degrees or less; and a non-aqueous cosmetic composition containing the same.

도면번역
도 10
110, 120, 130 분리: Separation
도 14
유전자 mixture: Gene Mixture
도 15
시험군: Test Group
대조군: Control Group

8 Claims, 9 Drawing Sheets

[Fig. 1]
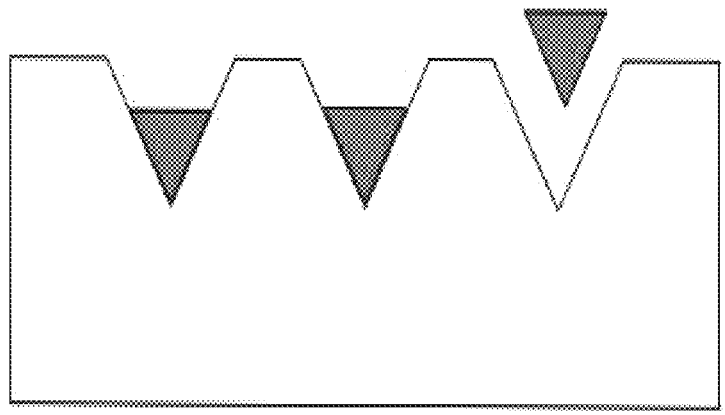
[Fig. 2]
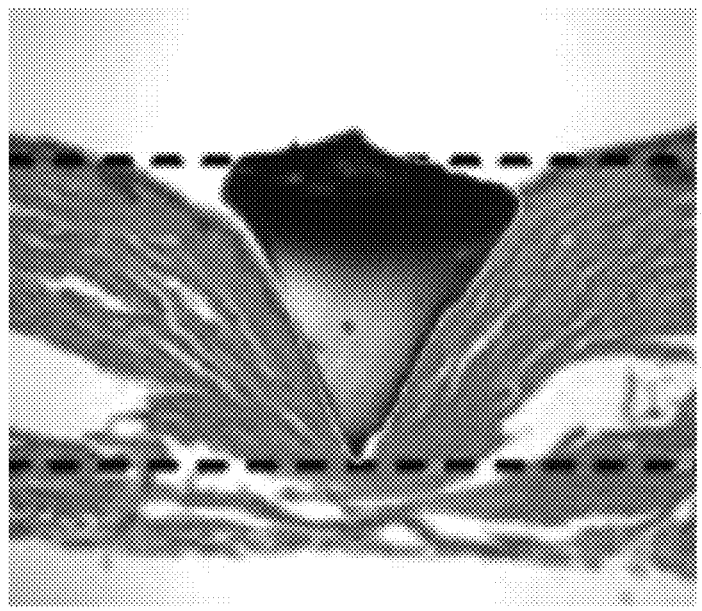

[Fig. 3]
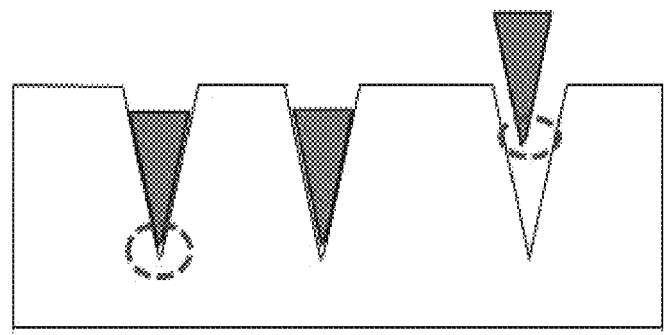
[Fig. 4]
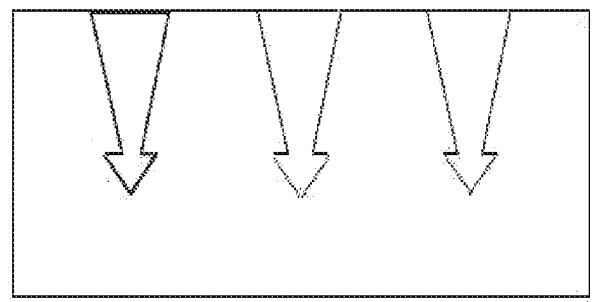
[Fig. 5]
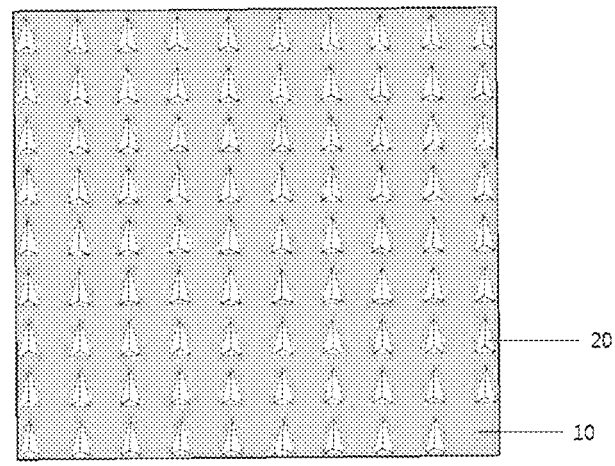

[Fig. 6]
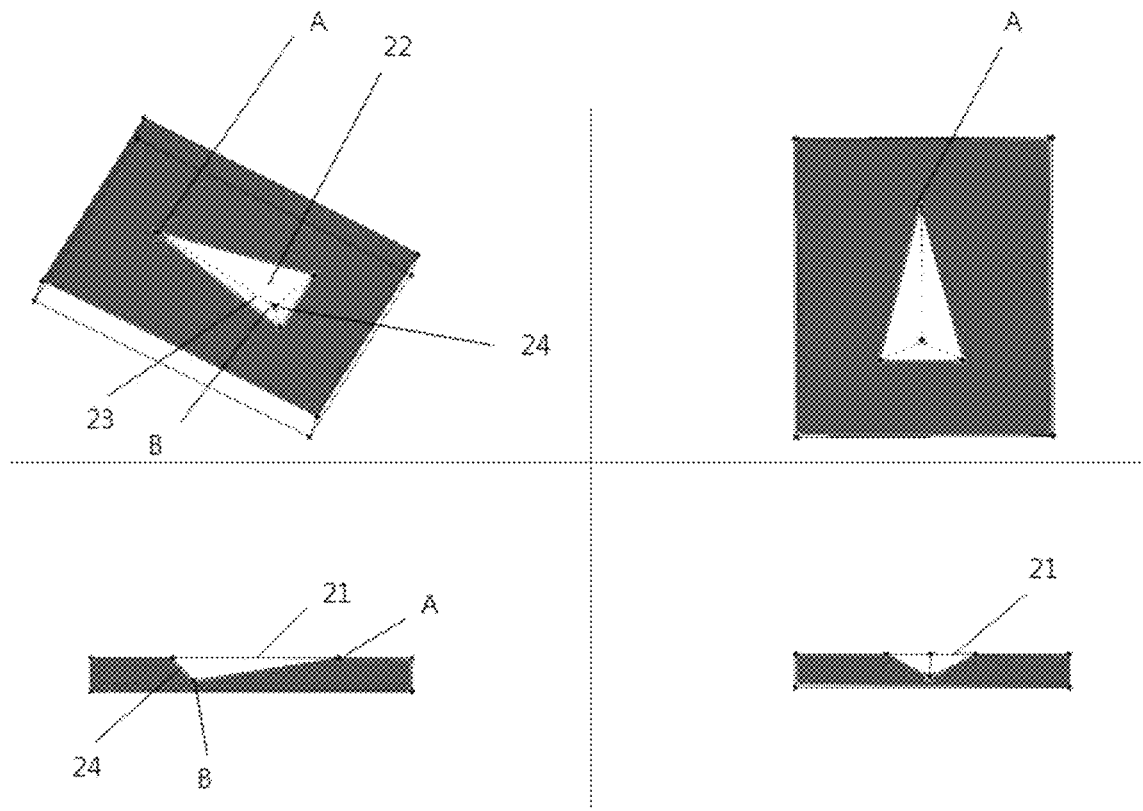
[Fig. 7]
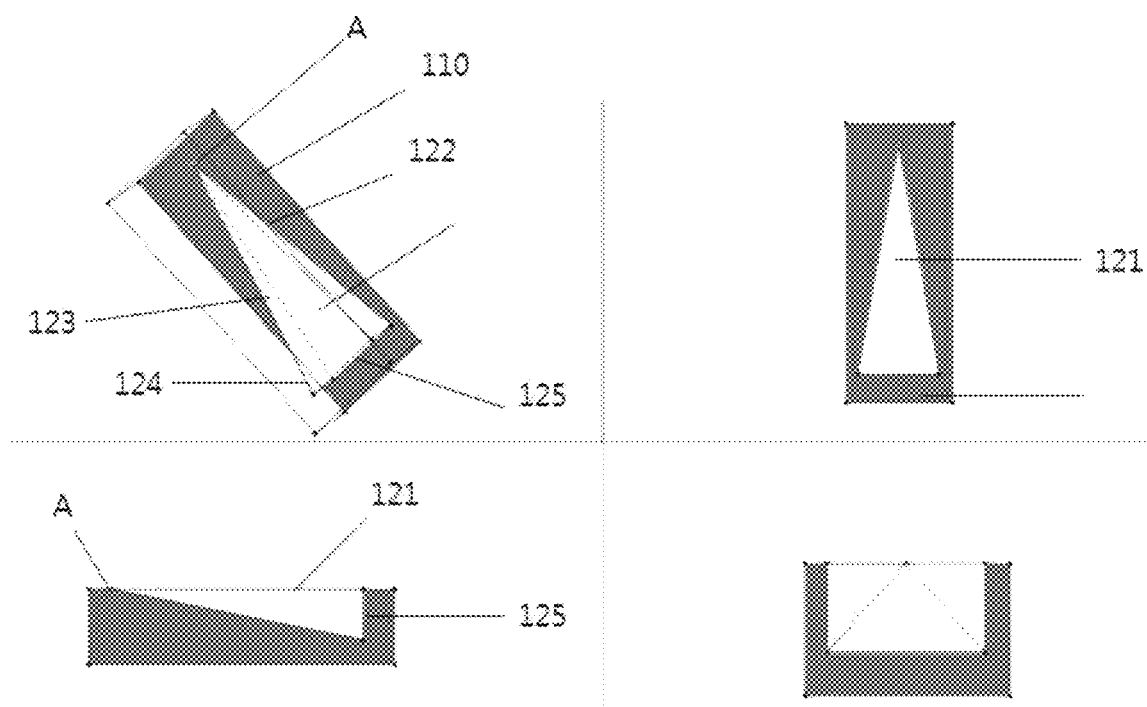

[Fig. 8]
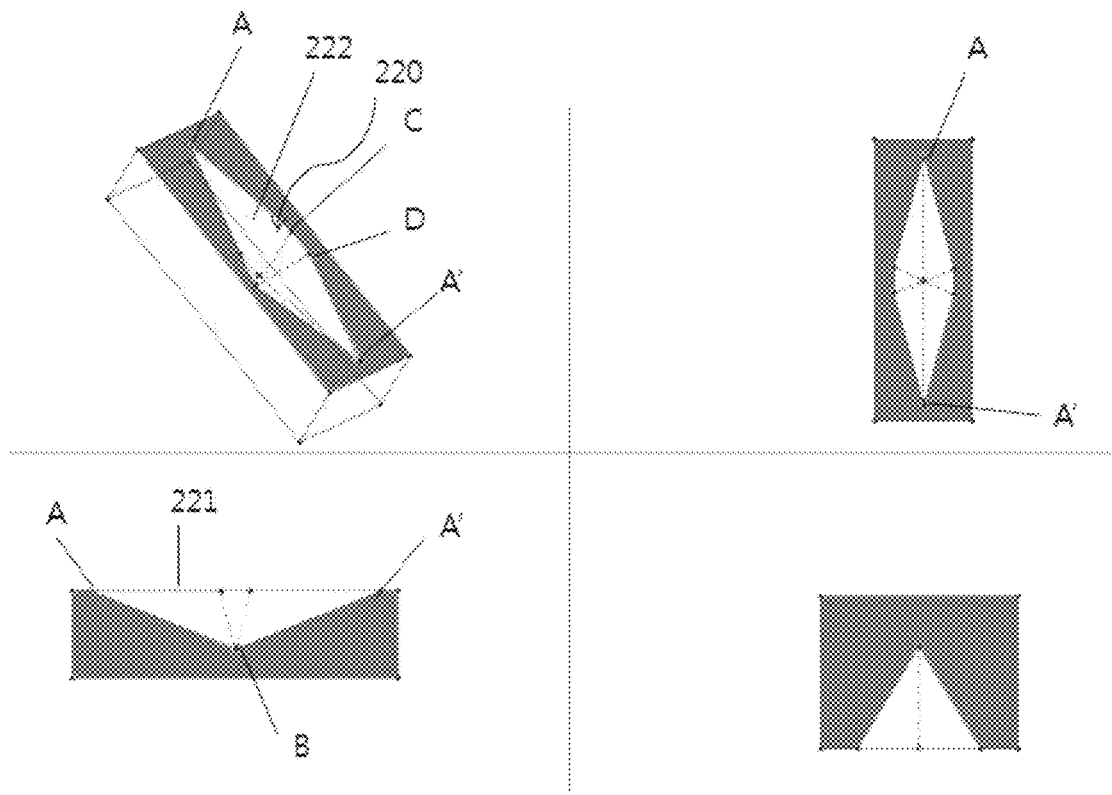
[Fig. 9]
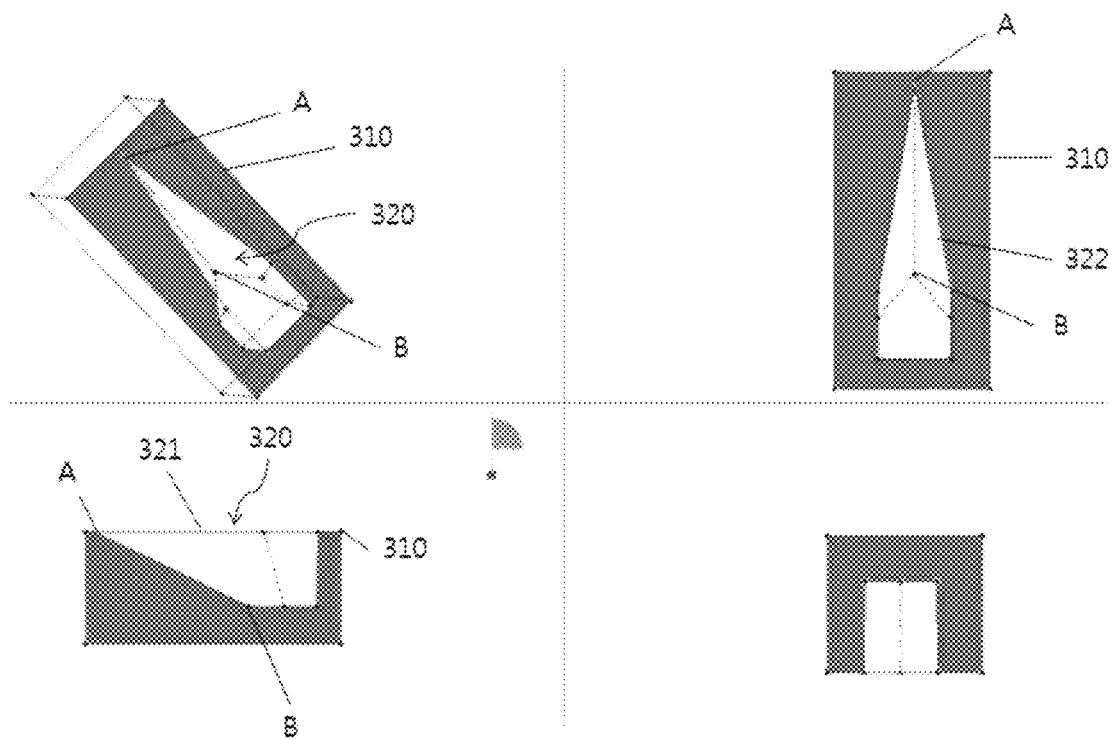

[Fig. 10]
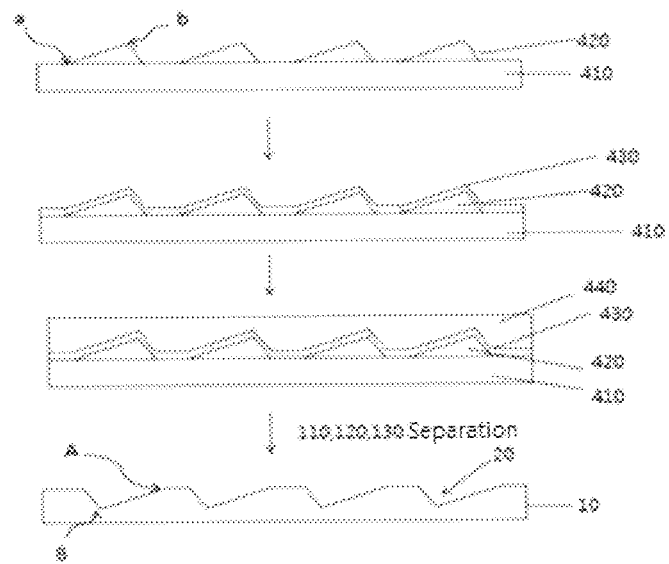
[Fig. 11]
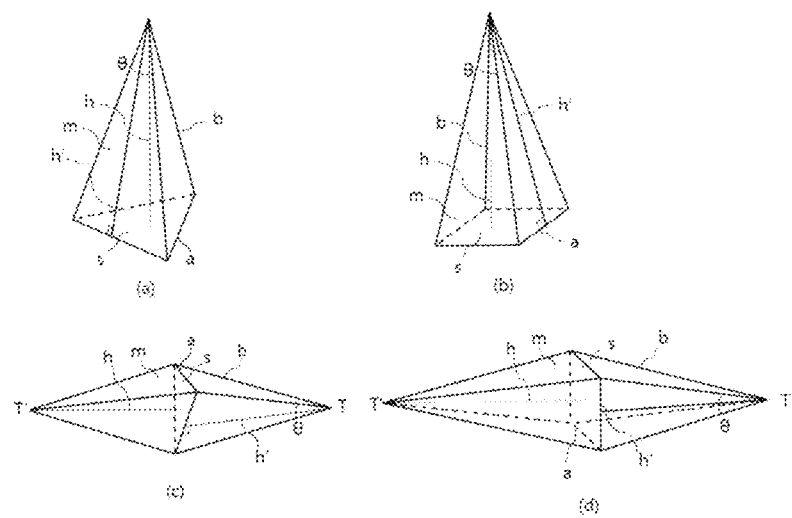

[Fig. 12]
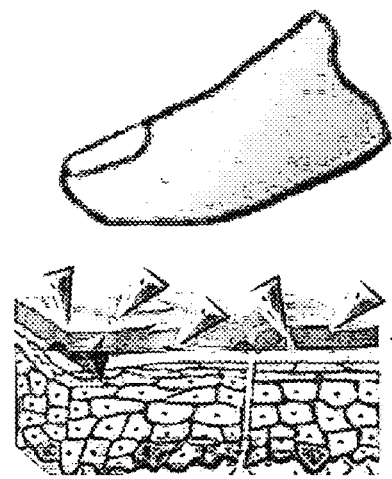
[Fig. 13]
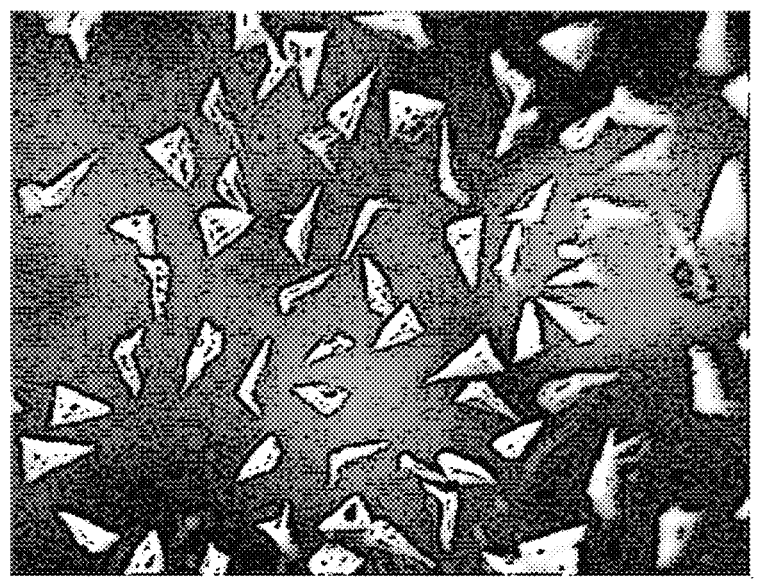

[Fig. 14]
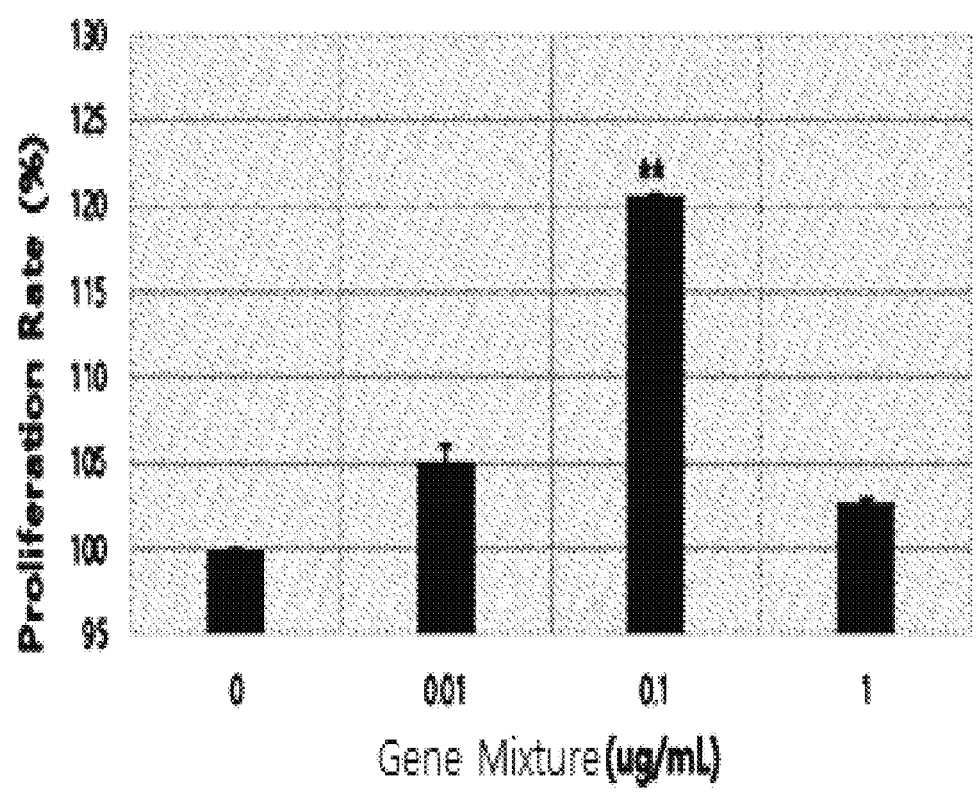

[Fig. 15]
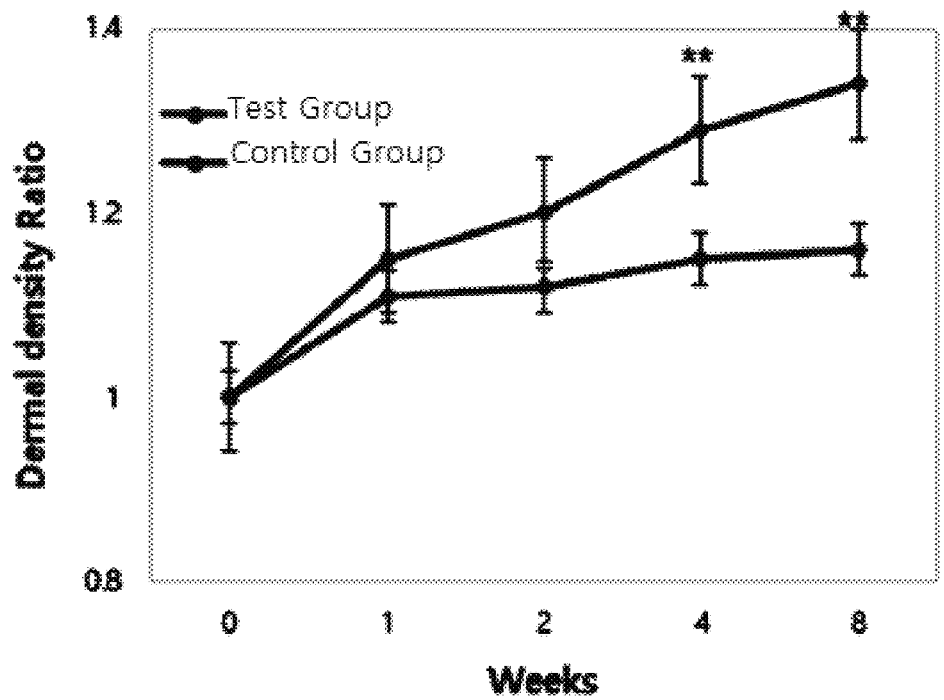
[Fig. 16]
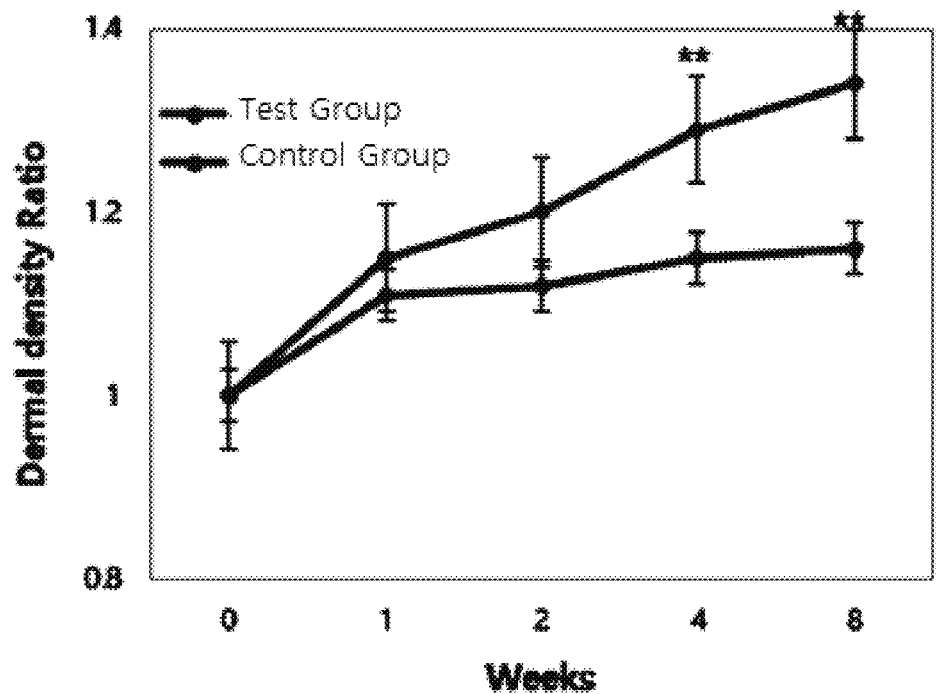

[Fig. 17]
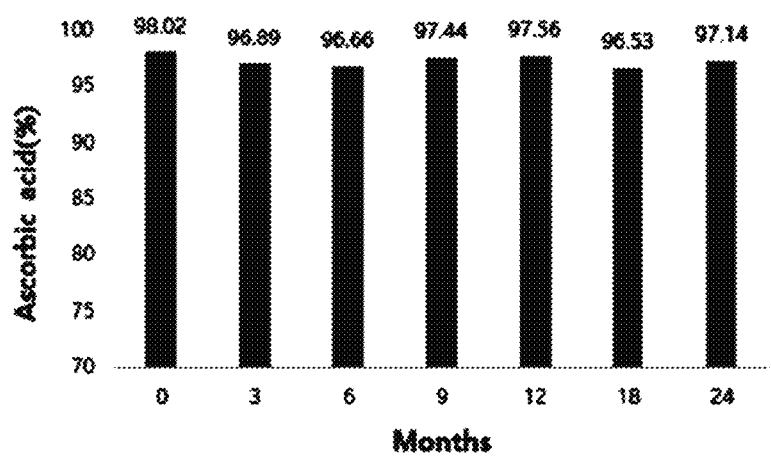

WATER-SOLUBLE MICRONEEDLE SPICULES AND NON-AQUEOUS COSMETIC COMPOSITION CONTAINING THE SAME

CROSS-REFERENCE TO RELATED APPLICATIONS

This application is a U.S. national stage filing under 35 U.S.C. § 371 of International Application No. PCT/KR2016/013634 filed Nov. 24, 2016 entitled "Water-Soluble Microneedle Spicules and Non-Aqueous Cosmetic Composition Containing the Same," which claims priority to and benefit of Korean Application No. 10-2015-0165847 filed Nov. 25, 2015, entitled "Water-Soluble Microneedle Spicules and Non-Aqueous Cosmetic Composition Containing the Same," and claims priority to and benefit of Korean Application No. 10-2016-0157312 filed Nov. 24, 2016, entitled "Water-Soluble Microneedle Spicules and Non-Aqueous Cosmetic Composition Containing the Same." The contents of each of these applications are hereby incorporated herein by reference in their entireties.

TECHNICAL FIELD

The present invention relates to water-soluble microneedle spicules for scrubs and a non-aqueous cosmetic composition containing the same. More specifically, the present invention relates to water-soluble microneedle spicules for scrubs, which are in the shape of a triangular pyramid or sexangular pyramid and characterized in that at least any one among the interior angles of the pyramid base of the spicules for scrubs is 90 degrees or less; and a non-aqueous cosmetic composition containing the same.

Additionally, the present invention relates to a non-aqueous cosmetic composition containing a water-soluble microneedle spicule for scrubs, in which the spicule is a water-soluble microneedle spicule containing a water-labile physiologically-active material such as a polypeptide, oligopeptide, cell culture filtrate, DNA fragment, RNA fragment, or water-soluble antioxidant, in the shape of a triangular pyramid or sexangular pyramid, in which at least any one among the interior angles of the polyangular pyramid base of the water-soluble microneedle spicule is 90 degrees or less.

More specifically, the present invention relates to a non-aqueous cosmetic composition containing a water-soluble microneedle spicule for scrubs in an amount of 0.01 wt % to 15 wt %, in which the spicule is a water-soluble microneedle spicule, in the shape of a triangular pyramid or sexangular pyramid, containing a component which is unstable in the presence of water and thus its physiological activity is reduced, such as a polypeptide physiologically-active material or oligopeptide physiologically-active material obtained by synthesis or biosynthesis or by genetic recombinant technology, a cell culture filtrate obtained by culturing useful cells such as stem cells, etc., DNA or RNA fragments or mixture of gene fragments extracted from plants and animals, water-soluble antioxidants such as vitamin C, etc., in which at least any one among the interior angles of the polyangular pyramid base of the spicule is 90 degrees or less.

BACKGROUND ART

Methods which deliver an effective material such as a skin cosmetic component or drug to the skin or attach a pack, patch, etc. containing an effective material to the skin thereby transferring the effective material to the skin have advantages in that they can continuously deliver an effective material and have a less pain on the skin, and they are small and simple.

However, since the stratum corneum on the outermost part of the skin having a thickness of 10 μm to 60 μm prevents penetration of foreign materials into the body, the skin penetration rate of the active ingredient is very low. In particular, when the active ingredient is hydrophilic or has a high molecular weight, its skin delivery rate is further lowered.

Therefore, for an effective delivery of an effective material to the skin, an injection method using an injection needle has been conventionally used.

However, since the diameter of a conventional needle is in the range of a few millimeters and its length is in the range of a few centimeters, the injection needle stimulates a large number of nodules present in the skin, thus causing considerable pain.

Additionally, injection needles have a disadvantage in that they are generally available only in hospitals or professional skin care institutions, and thus normal people cannot use them themselves.

In order to overcome the disadvantages in the methods of delivering an effective material through the conventional art using these needles, microneedles having a diameter of several tens of micrometers to several hundreds of micrometers and a length of several tens to several thousands of micrometers have been developed.

These microneedles were applied to the keratin layer of the skin while being fixed to the support so as to form micropores in the keratin layer of the skin, the active ingredient could be delivered to the skin through the thus-formed micropores.

Additionally, since microneedles are short in length, they cannot penetrate deep into the dermal layer where the nerves are distributed, thus not causing pain.

Even if microneedles can penetrate into the dermal layer, the diameter of these microneedles have a smaller diameter and shorter length compared to those of the conventional injection needles, and thus have a smaller number of stimulating pain spots thereby significantly reducing pain.

International Patent Application (PCT) Publication No. WO 02/47555 discloses a device for treating the skin of a subject, the device including a head defining a convex head surface, characterized in that a plurality of spaced pins are set in the head and protrude a predetermined distance from the head surface, and a method for applying a skin cosmetic material after forming minute clefts in the upper epidermis.

Additionally, U.S. Pat. No. 5,487,726 discloses a vaccine applicator system which includes application of a vaccine to the skin and formation of micro-holes on the keratin layer of the skin of the skin in which the vaccine is applied using a device equipped with a spike.

However, according to International Patent Application (PCT) Publication No. WO 02/47555 and U.S. Pat. No. 5,487,726, the step of drug application to the skin and the step of forming the micropores in the keratin layer of the skin are performed separately, thus causing inconvenience to users.

Another method to facilitate an easier penetration of an effective material through the keratin layer of the skin is to use skin exfoliating cosmetics and apply skin cosmetic materials to the skin.

Skin exfoliating cosmetics remove keratin by mechanical friction between a scrubbing agent and the keratin layer of the skin mainly using a water-insoluble scrubbing agent that can physically remove keratin.

Accordingly, it is necessary to remove the keratin using such skin exfoliating cosmetics, surely rinse the water-insoluble scrubbing agent, and then apply an effective material to the skin.

Additionally, in a case where the scrubbing agent gets into the eye during its application, there are problems in that the removal of the scrubbing agent is not easy, and the user may feel the presence of foreign materials, and the cornea may be damaged by rubbing the eyes with the hands.

KR Patent No. 10-1206985 discloses a method to achieve the effects of skin moisturization, promotion of blood circulation, and removal of skin wastes and keratin by containing water-soluble scrub spicules to the cosmetics. However, these cosmetics are cosmetic compositions for a massage, which are not intended to deliver the skin of an active ingredient but simply contain a large amount of sugar powder for skin scrub purposes.

Additionally, the sugar scrub powder described in KR Patent No. 10-1206985 has disadvantages in that the sugar particles generally have 6 or more surfaces and thus the angles made by each surface are large, and the edges are blunt, making the scrub effect difficult to increase.

In order to overcome these disadvantages of the prior art described above, the present inventors have filed a patent application with regard to microneedle spicules in the shape of a tetrahedron or pentahedron pyramid (a triangular pyramid or quadrangular pyramid) (KR Patent Application No. 10-2014-0007338).

The microneedle spicules can effectively promote the penetration of the effective component of skin cosmetics through the keratin layer because each vertex of the polyhedron can form micropores in the keratin or remove part of the keratin.

FIG. 1 is a schematic diagram illustrating a method for preparing microneedle spicules described in Korea Patent Application No. 10-2014-0007338. FIG. 1 shows a method for preparing scrub spicules, in which the ratio between the height from the sharp vertex to the base of a microneedle in the shape of a polyangular pyramid and a diagonal length of the base of the pyramid (hereinafter, abbreviated as an aspect ratio) is 1:1.

However, when the microneedle spicules prepared by the method of FIG. 1 is applied to the skin, there is a problem in that the ratio of protrusions exhibiting an acute angle of 90 degrees or less is lowered, thereby lowering the efficiency of microchannel formation in the keratin layer of the skin.

FIG. 3 shows a case where the aspect ratio exceeds 1:1. As in FIG. 3, when the aspect ratio becomes large, there is a problem in that when filling a water-soluble material that forms microneedle spicules into a mold engraved with a polyangular pyramid for the preparation of scrub spicules, air is difficult to escape therefrom and the water-soluble material cannot be completely filled.

Additionally, when the aspect ratio becomes large, the contact area between the negatively-engraved mold and the formed microneedle spicules becomes relatively enlarged and thus it is difficult to separate the microneedle spicules formed from the mold.

For these reasons, when an attempt was made to form microneedle spicules in the shape of a sharper polyangular pyramid by increasing the aspect ratio, which is the ratio between a diagonal length of the base of a polyangular pyramid shape and a height from the base to the sharp vertex, there were problems in that defective products where the microneedle was not perfectly formed due to defective filling or the molding process was delayed due to difficulty in mold release.

Meanwhile, recently with the rapid progress of aging population, the anti-aging cosmetics have been spotlighted, and bio-cosmetics containing polypeptide growth factor, oligopeptide growth factor, cell culture filtrate, gene fragment, antioxidant component, etc. are being rapidly developed.

As prior arts related to bio-cosmetics containing a polypeptide growth factor or oligopeptide growth factor, KR Patent Nos. 10-0433373, 10-1289062, 10-2013-0024316, etc. are disclosed.

Additionally, as prior arts related to bio-cosmetics containing a stem cell culture filtrate, KR Patent No. 10-1063299, KR Patent No. 10-1047873, KR Patent Application Publication No. 10-2010-0098298, etc. are disclosed.

Additionally, as prior arts related to bio-cosmetics containing a gene fragment KR Patent Nos. 10-1662438, 10-0986603, etc. are disclosed.

Additionally, as prior arts related to bio-cosmetics containing an antioxidant component such as vitamin C, KR Patent Nos. 10-1339369, 10-0819173, etc. are disclosed.

However, the stability of physiological activity of polypeptides, oligopeptides, cell culture filtrates, DNA fragments, RNA fragments, and water-soluble antioxidants are influenced by the surrounding physical or chemical environment, and in particular, when water is present, they easily undergo hydrolysis or denaturation, it is not easy to stably maintain the physiological activity when these materials are added to a cosmetic composition.

In order to protect water-soluble physiologically-active ingredients which are susceptible to such hydrolysis or denaturation and maintain their activity for a long period of time, methods of promoting stability by removing water through freeze-drying or drying after purification, or liposome methods which prevent the physiological activity from contacting the liposomes in the aqueous solution by wrapping the physiological activity in lipids.

Freeze-drying techniques can be applied to raw materials, but it is not easy to apply these techniques to general formulations for finished cosmetic products. The liposome method can provide a stabilizing effect to some extent, but the method has a problem in that it is difficult to maintain the stability for 6 months or longer.

For example, epidermal growth factor (EGF), an oligopeptide widely used in bio-cosmetics, undergoes a decrease of its physiological activity not only at room temperature but also even during the storage in a refrigerator, when it is stored in an aqueous solution for a long period of time. Therefore, it is well known that the material is difficult to formulate for commercialization which requires a shelf-life period.

EP Patent Application Publication Nos. 205,051 and 267, 015, U.S. Pat. No. 4,717,717, KR Patent Nos. 10-1996-0013439, 10-0570358, 10-0752990, etc. disclose compositions which can increase stability using surfactants, lipids, cellulose polymers, metal cations, nano-vectors, nano-liposomes, etc.

However, even using these conventional techniques, it is not easy to maintain the activity of oligopeptide epithelial growth factor (EGF) in cosmetics at room temperature circulation conditions, non-sterile conditions, and aqueous conditions.

In particular, since epidermal growth factor (EGF) is added to cosmetics at a concentration lower than 10 ppm, which is a level allowed to cosmetics, it is almost impossible to maintain the physiological activity of epithelial growth factor (EGF) during the period of storage, distribution, and use.

Due to high molecular weight, oligopeptides, polypeptides, DNA fragments, and RNA fragments cannot penetrate into the skin even when are added to cosmetics and thus they can hardly have effects. Therefore, for the enhancement of the effectiveness of bio-cosmetics containing these ingredients, special techniques must be applied.

For example, the use of a peptide fusion technique to attach a specific site (e.g., protein transduction domain (PTD)) to an oligopeptide or polypeptide, application of a liposome technology to wrap the skin in lipids to help skin absorption, and a method to link a microneedle therapy system (MTS) to cosmetics are mainly used.

To solve the above problems, the present inventors have invented a non-aqueous cosmetic composition containing a water-soluble microneedle spicule, in which the water-soluble microneedle spicule is comprised of a water-soluble microneedle spicule in a polyangular shape containing a water-labile physiologically-active material such as a polypeptide, oligopeptide, cell culture filtrate, DNA fragment, RNA fragment, or water-soluble antioxidant, and in which at least any one among the interior angles of the vertices of the microneedle in a polyangular shape is 90 degrees or less thus having an improved ratio of an acute angle. As a result, they could effectively deliver the composition to the skin while stably maintaining the activity of the active ingredient stable for a long period of time and removing the keratin layer.

Additionally, the present inventors have confirmed that when the non-aqueous cosmetic composition containing the water-soluble microneedle spicule having an improved ratio of an acute angle was applied to the skin and scrubbed, followed by the dissolution of the water-soluble microneedle spicule using an aqueous cosmetic such as an emulsion, a physiologically-active material such as a polypeptide, oligopeptide, cell culture filtrate, DNA fragment, RNA fragment, or antioxidant contained in the water-soluble spicule and hyaluronic acid were stably maintained until use and they were also effectively penetrated deep into the skin, thereby completing the present invention.

As used herein, the oligopeptide and polypeptide is a material in which two or more amino acids are polymerized by condensation and is defined as a peptide polymer having at least a dipeptide. This material can be made by synthetic, biosynthetic, and recombinant protein technology known in the art.

As used herein, the DNA fragment, RNA fragment, or gene fragment mixture is a material extracted from plants such as broccoli petals, rose petals, pine pollen, etc., microorganisms as yeasts, etc., semen and testicles of animals, etc.

The water-soluble microneedle spicule of the present invention is comprised of a water-soluble material, such as a polysaccharide, monosaccharide, oligosaccharide, and salt, which is readily dissolved when in contact with water, and it is a spicule in the shape of a triangular pyramid or sexangular pyramid in which at least any one among the interior angles of the pyramid base of the spicule is 90 degrees or less.

The non-aqueous cosmetic composition of the present invention may be a non-aqueous composition containing a water-soluble microneedle spicule in a polyangular shape, in which the microneedle spicule is a water-soluble microneedle spicule containing a water-labile physiologically-active material such as a polypeptide, oligopeptide, cell culture filtrate, DNA fragment, RNA fragment, or water-soluble antioxidant, in the shape of a triangular pyramid or sexangular pyramid, in which at least any one among the interior angles of the polyangular pyramid base of the water-soluble microneedle spicule is 90 degrees or less; or may be a non-aqueous composition containing only microneedle spicule, without containing a water-labile physiologically-active material such as the polypeptide, oligopeptide, cell culture filtrate, DNA fragment, RNA fragment, or water-soluble antioxidant; and may be a non-aqueous cosmetic composition in which the above two kinds of water-soluble microneedle spicules are mixed together.

Additionally, the non-aqueous cosmetic composition of the present invention may further contain a spicule comprised of various water-soluble materials in various shapes, not corresponding to the water-soluble microneedle spicule in a polyangular shape of the present invention.

DISCLOSURE

Technical Problem

Accordingly, an object of the present invention is to provide a microneedle spicule for scrubs in a novel shape with a higher ratio of sharper acute angle without increasing the above-described aspect ratio, a preparation method thereof, and a mold used for the preparation method.

Additionally, another object of the present invention is to provide a non-aqueous cosmetic composition which can prevent a phenomenon of the loss of mechanical strength required as a scrub spicule due to the dissolution or swelling of a water-soluble microneedle spicule by a non-aqueous dispersion medium, by preparing microneedle spicules for scrubs, which remove part of the keratin layer of the skin through the mechanical friction with the keratin layer of the skin, using water-soluble materials followed by dispersion the same in the non-aqueous dispersion medium.

Additionally, still another object of the present invention is to provide a water-soluble microneedle spicule for scrubs, in which the spicule is a water-soluble microneedle spicule for scrubs in the shape of a triangular pyramid or sexangular pyramid in which at least any one among the interior angles of the pyramid base of the spicule is 90 degrees or less, so as to maximize the scrub effect of the keratin layer of the skin by forming more acute angles to the water-soluble spicule for scrubs.

Still another object of the present invention is to provide a water-soluble microneedle spicule for scrubs containing an effective material capable of inducing a cosmetic or pharmacological effect on the skin, in which the spicule is a water-soluble microneedle spicule for scrubs in the shape of a triangular pyramid or sexangular pyramid in which at least any one among the interior angles of the polyangular pyramid base of the spicule is 90 degrees or less, so as to maximize the scrub effect of the keratin layer of the skin by forming more acute angles to the water-soluble spicule for scrubs and maximize the skin transfer effect of the effective material through the exfoliated channel.

Additionally, still another object of the present invention is to provide a non-aqueous cosmetic composition containing a water-soluble microneedle spicule for scrubs, in which the spicule is a water-soluble microneedle spicule for scrubs in the shape of a triangular pyramid or sexangular pyramid in which at least any one among the interior angles of the polyangular pyramid base of the spicule is 90 degrees or less, so as to maximize the scrub effect of the keratin layer of the skin by forming more acute angles to the water-soluble spicule for scrubs and maximize the skin transfer effect of the effective material through the exfoliated channel.

Additionally, still another object of the present invention is to provide a non-aqueous cosmetic composition, which simultaneously contains both a water-soluble microneedle spicule for scrubs, in which the spicule is a water-soluble microneedle spicule for scrubs in the shape of a triangular pyramid or sexangular pyramid in which at least any one among the interior angles of the polyangular pyramid base of the spicule is 90 degrees or less; and a water-soluble microneedle spicule in which an effective material capable of inducing a cosmetic or pharmacological effect is incorporated to the water-soluble microneedle spicule having such a characteristic, so as to maximize the scrub effect of the keratin layer of the skin by forming more acute angles to the water-soluble particles for scrubs and maximize the skin transfer effect of the effective material through the exfoliated channel.

Additionally, still another object of the present invention is to provide a cosmetic composition which further contains water-soluble spicules excluded in the present invention while containing separately or simultaneously the water-soluble spicules for scrubs of the present invention described above.

Technical Solution

The basic object of the present invention can be achieved by providing a water-soluble microneedle spicule for scrubs, in which the spicule is in the shape of a triangular pyramid or sexangular pyramid in which at least any one among the interior angles of the polyangular pyramid base of the spicule is 90 degrees or less and the height from the base to the vertex is 1 to 2 times greater than the diagonal length of the base.

Another object of the present invention can be achieved by providing a water-soluble microneedle spicule for scrubs containing an effective material capable of inducing a cosmetic or pharmacological effect to the skin, in which the spicule is in the shape of a triangular pyramid or sexangular pyramid in which at least any one among the interior angles of the polyangular pyramid base of the spicule is 90 degrees or less and the height from the base to the vertex is 1 to 2 times greater than the diagonal length of the base.

Still another object of the present invention can be achieved by providing a non-aqueous cosmetic composition containing a water-soluble microneedle spicule for scrubs, in which the spicule is in the shape of a triangular pyramid or sexangular pyramid in which at least any one among the interior angles of the polyangular pyramid base of the spicule is 90 degrees or less and the height from the base to the vertex is 1 to 2 times greater than the diagonal length of the base.

Still another object of the present invention can be achieved by providing a non-aqueous cosmetic composition, which simultaneously contains a water-soluble microneedle spicule for scrubs, in which the spicule is in the shape of a triangular pyramid or sexangular pyramid in which at least any one among the interior angles of the polyangular pyramid base of the spicule is 90 degrees or less and the height from the base to the vertex is 1 to 2 times greater than the diagonal length of the base; and a water-soluble microneedle spicule in which an effective material capable of inducing a cosmetic or pharmacological effect is incorporated to the water-soluble microneedle spicule having such a characteristic.

Still another object of the present invention can be achieved by providing a mold for forming a microneedle shape, in which the mold is one where the microneedle in a polyangular pyramid shape comprised of a triangular pyramid or sexangular pyramid is negatively-engraved, in which at least any one among the interior angles of the engraved polyangular pyramid base of the spicule is 90 degrees or less and the height from the base to the vertex is 1 to 2 times greater than the diagonal length of the base, In the method for preparing microneedle of the present invention, the vertex part of the microneedle polyangular pyramid (hereinafter abbreviated as a tip) is formed in a horizontal direction with the base portion of the mold, the depth of the engraved area is not further deepened but the surface area exposed to the outside becomes enlarged.

Accordingly, with regard to the microneedle spicule of the present invention, the residual air can easily be released and the needle can also be easily separated from the mold compared to the conventional preparation method.

Additionally, even in the microneedle spicule where a bump is formed around the tip, the release is possible by forming a microneedle in the horizontal direction according to the method of the present invention, and the microneedle spicule having a bump formed around the tip can be prepared.

The microneedle spicule of the present invention effectively forms microchannels on the skin in spite of the skin's deformation, thereby enhancing the skin delivery efficiency of the active ingredient.

Additionally, the present invention provides an easy method for preparing a microneedle as described above, thereby enabling mass production and commercialization of the microneedles.

DESCRIPTION OF DRAWINGS

FIG. 1 is a schematic diagram showing a method for preparing microneedles as described in KR Patent Application Publication No. 10-2014-0007338, a prior art.

FIG. 2 is an image showing the application of the microneedle prepared in FIG. 1 to the skin.

FIG. 3 is a schematic diagram showing a case where microneedles are prepared with the aspect ratio (the ratio between the diagonal length on the base of a polyangular pyramid and the length from the base to the tip) exceeding 1:1 by the method of FIG. 1.

FIG. 4 is a schematic diagram showing a prior art case in which microneedles having a bump around a tip is prepared by a molding method of vertical direction filling as shown in FIG. 1.

FIG. 5 shows a mold for preparing microneedles according to the present invention.

FIG. 6 shows a perspective view, a plan view, and a side view of an enlarged structure of a microneedle in a negatively-engraved shape formed in a mold.

FIG. 7 shows a mold in which the microneedle 120 having a quadrangular pyramid shape was formed by a negative engraving.

FIG. 8 is an illustrative embodiment of a polyangular or modified polyangular pyramid having two needle tips (A, A').

FIG. 9 is an illustrative embodiment of a modified polyangular pyramid.

FIG. 10 shows a method of preparing a mold for microneedes with a polyangular pyramid shape of FIG. 5.

FIG. 11 shows illustrative embodiments of the microneedles with a polyangular pyramid shape of the present invention.

FIG. 12 is a conceptual diagram showing the application of the non-aqueous cosmetic composition of the present invention.

FIG. 13 is an image under 30-fold magnification showing water-soluble microneedle spicules in the shape of a polyangular pyramid of the present invention.

FIG. 14 is a graph showing the cell proliferation effect of physiologically- active components in the shape of a polyangular pyramid of the present invention.

FIG. 15 is a graph showing statistical comparison results with regard to the effect of changes in skin density of the non-aqueous cosmetic composition of the present invention.

FIG. 16 is a graph showing statistical comparison results with regard to the effect of changes in skin density of the non-aqueous cosmetic composition of the present invention.

FIG. 17 shows the results of a HPLC stability test of the non-aqueous cosmetic composition of the present invention.

Hereinafter, the microneedle spicule of the present invention will be described in more detail with reference to the accompanying drawings.

FIG. 4 represents a mold for preparing microneedle spicules and FIG. 5 is an enlarged perspective view, a plan view, and a side view of a needle structure with a negative engraving formed on a mold.

Referring to FIGS. 4 and 5, the mold for preparing the microneeds of the present invention includes a base part 10 and a negatively-engraved needle shape 20.

There is no particular limitation on the base part 10. For example, a metal, polypropylene, polyethylene, polyacrylate, or polycarbonate may be used as the base part.

The needle shape 20 is formed by negative engraving in the base part. The needle shape 20 is formed with a polygonal structure having a tip or vertex at negatively engraved in the base part.

Referring to FIG. 5, the tetrahedral structure of the needle shape 20 is formed by negative engraving. The shape of the tetrahedral negatively-engraved needle 20 is formed by the negatively-engraved surfaces 22, 23, and 24 on the inside of the base part while having the surface of the base part exposed by negative engraving as one surface 21.

In the molds for preparing the conventional needle structure shown in FIGS. 1 to 3, the negative engraving for needles is formed to be negatively engraved to be perpendicular to the base part. However, in the present invention, the needles with a negatively-engraved shape are formed in a direction horizontal to the base part 10. Preferably, the needle tip (A) with a negatively-engraved shape is disposed on the surface of the base part.

In particular, the tip (A) represents a vertex having the longest height among the vertices with the structure formed by negative engraving. The height of the vertex is the vertical distance between each vertex and the opposing surface.

The height of the vertex tip may be 1.375 times or more compared to the length of the diagonal length on the base, and preferably, 1.375 to 10 times, and more preferably 1.5 to 5 times.

Alternatively, the ratio of the base to the edge of the triangle 21 located on the surface of the base part among the faces forming the vertex tip may be in the range of 1:1.375 times or more, preferably 1:1.375 to 10 times, and more preferably 1:1.5 to 5 times.

The angle of the vertex tip formed on the surface of the base part may be 40 degrees or less. The angle of the tip may be the vertex angle of the triangle 21.

FIGS. 3 and 5 can prepare needle spicules having the same tetrahedral shape, however, in the case of FIG. 3, the needle shape is negatively engraved to be perpendicular to the base surface, and in FIG. 5, the needle shape is negatively engraved to be horizontal to the base surface.

In the case of FIG. 5, the surface which includes the needle tip (A) with the longest length is formed by negative-engraving on the surface, whereas the tip (B) with a relatively short length is negatively engraved to be perpendicular to the surface of the base part.

Accordingly, compared to FIG. 3, the mold for preparing the microneedle spicule of the present invention does not necessitate the formation of a needle tip shape to be formed deep into the inside of the base part. Additionally, since the surface 21 including the needle tip (A) is negatively engraved on the surface of the base part, the surface are being exposed becomes larger.

Accordingly, the microneedle spicule of the present invention has advantages in that the release of residual air becomes easier and the separation of the needle is much easier compared to the convention method with a perpendicular structure. Additionally, in the case of the microneedle where a bump is formed, when the microneedle is formed in a horizontal direction as in the present invention, it is possible to release and microneedles in which needle tips are formed in both directions can be prepared.

FIG. 7 shows images in which the needle shapes 120 are formed in a quadrangular pyramid structure by negative engraving. The needle shapes 120 with the shape of negatively-engraved quadrangular pyramid are formed by the three negatively-engraved surfaces 122, 123, and 124 exposed to the inside of the surface of the flat base part and the surface of the base 125.

The tip (A) of the needle shape 120 is the vertex of the quadrangular pyramid.

As in the tetrahedral structure of FIG. 5, the needle shape 120 of the present invention is horizontally formed on the base part 110. Preferably, if the needle shape is formed so that the vertex of the quadrangular pyramid can be positioned on the surface of the base part, it is not necessary to form a negatively-engraved groove deep into the inside of the base part.

As described above, in the present invention, the needle shape is formed to have a polyhedral structure on the base part, and the polyhedral structure formed by negative engraving may be a polyangular pyramid having at least two vertices or tips, or a modified polyangular pyramid in which the polyangular pyramid and angular columns are bound together.

The negatively-engraved polyhedral structure of the present invention may be a polyhedral structure provided with at least two vertices located on the surface of the base part. The length of the at least two vertices may be the same or different with each other.

FIG. 8 is an illustrative embodiment of a polyangular or modified polyangular pyramid having two needle tips (A, A'). The negatively-engraved needle shape 220 is formed by the surface of the base part 221 exposed by negative engraving and the negatively-engraved surfaces inside of the base part (222 and others).

As shown in FIG. 8, in the present invention, the polyhedrals with a structure where two polyangular pyramids are attached together can be formed to the base part by negative engraving. The diangular pyramids are negatively engraved in a structure where the parts of the base surface of the polyangular pyramid are attached together and two vertices are adjusted to be disposed on the surface of the base part thereby generating a structure where the negatively-engraved polyhedral shape can be horizontally formed on the flat base surface. The needle shape of FIG. 8 is negatively engraved so that the two needle tips can be positioned on the surface of the base.

Although the length of the two needle tips is the same in FIG. 8, the needles may be prepared such that any one needle tip may be longer than the other. The length of the tips (A, A') is greater than the height of the vertex D, which is formed in a vertical direction inside of the base part.

The needle tips of FIG. 8 may be formed in opposite directions on the surface of the base part. Microneedles being prepared from the polyhedral negatively-engraved structure of microneedles having a bi-directional tip, as shown in FIG. 8, have many sharp edges and thus it is very easy for them to form microchannels on the skin.

FIG. 9 is an illustrative embodiment of a modified polyangular pyramid. FIG. 9 has a single needle tip (A) and shows a negatively-engraved shape of needle spicules in which polyhedrals are attached to the quadrangular columns. The shape of negatively-engraved needles 320 are formed by a surface 321 of a base part 310 formed by negative engraving, and negatively-engraved surfaces (322 and others) inside of the base part.

Referring to FIG. 9, the needle tip (A) of polyangular pyramid is disposed on the surface of the base part 321. In the modified polyangular pyramid of FIG. 8, the vertex of the longest length is not negatively engraved to the base part vertically but is negatively engraved horizontally. Accordingly, it shows that the polyhedral structure does not have to be negatively engraved vertically deep into the base part.

The present invention includes a mold for microneedles in which a structure such as a bumped tip or a shape such as an anchor are negatively engraved horizontally. The shape such as an anchor may be negatively engraved horizontally by the method explained above (i.e., so that the needle tips can be disposed on the surface of the base part).

The shape such as an anchor as in the present invention is negatively engraved horizontally (see FIG. 3), the microneedle spicules can easily be released from the mold, unlike in FIG. 3.

FIG. 10 shows a method of preparing a mold for spicules of FIG. 4. Referring to FIG. 10, the method of preparing a mold for microneedles includes forming a positively-engraved polyhedral structure, forming a polymer or metal to a predetermined thickness, and separation and removal.

First, in the present invention, the positively-engraved polyhedral structure 420 having a needle vertex tip (a) is formed by a predetermined method. In the present invention, the vertex tip is configured to be disposed on the surface of the base part. The tip is the vertex having the longest length among the vertices of a polyhedron. Accordingly, FIG. 10b cannot be a tip in the present invention.

The method for forming a positively-engraved polyhedron (see: it is a tetrahedral structure in FIG. 10) on the substrate (base) includes: depositing a metal layer such as Cr, etc. on a glass substrate; transcribing a needle pattern on a metal layer using a needle-shaped mask; coating a photosensitive agent on the metal layer to a predetermined thickness; exposing or vertically exposing the ultraviolet ray according to the three-dimensional shape of needles; and removing the unexposed portions by etching.

The positively-engraved polyhedral structure may be formed with a photo-sensitive material known in the art.

In the above method, a polymer layer or metal layer 440 is formed on the polyhedral structure 420 to an appropriate thickness.

As the method for forming the metal layer to a predetermined thickness, a method of metal deposition known in the art may be used.

Additionally, the method of forming the metal layer to a predetermined thickness may be performed by electroplating.

For example, the method performs depositing a thin layer of a conductive metal 430 for electroplating on the positively-engraved polyhedral structure 420.

Then, the method may be able to perform the electroplating by transporting a mold-forming metal to a conductive metal substrate, in which the substrate is placed in an electrolyte aqueous solution to use as one electrode (+electrode) and the reference electrode as the other electrode (–electrode).

Referring to FIG. 10, after the electroplating, the substrate, the positively-engraved polyhedral structure 420, and the conductive metal 430 can be separated and removed from the metal for molding.

Referring to FIG. 10, the needle vertex tip (a) in the positively-engraved polyhedral structure 420 corresponds to the needle tip (A) in the negatively-engraved polyhedral structure 20, and the needle tip (A) is disposed on the surface of the base as described above.

The present invention relates to a method for preparing microneedles. As described above, the microneedles prepared in the present invention are of a polyhedral polyangular pyramid structure having at least one tip or vertex, and the needle is characterized in that the height of the tip is 1 to 2 times longer than the diagonal length in the base corresponding to the tip.

The microneedle of the present invention exhibits the function of spicules for scrubs that removes the keratin layer of the skin and thereby allows skin cosmetic materials or drugs to be delivered.

The method for preparing microneedles of the present invention includes: filling a mixed solution of a mixed solution in which a biocompatible material, water or a useful component material is dissolved into a negatively-engraved mold for preparing microneedles; obtaining microneedles by drying the mixed solution; and separating the microneedles from the negatively-engraved mold.

The biocompatible material may be selected from the group consisting of a polysaccharide, polyvinyl alcohol, carboxyvinyl polymer, chitosan, hyaluronic acid, cellulose polymer, and salt.

For the constituting elements of the water-soluble microneedle spicule of the present invention, any water-soluble material which can be used as a cosmetic component may be appropriate, however, it is appropriate to use least one component selected from polysaccharides, monosaccharides, oligosaccharides, and salts, and most preferably, the constituting element is comprised of hyaluronic acid, which is water-soluble and a constituting element of the skin.

The present invention, in order to stabilize water-labile physiologically-active components such as polypeptides, oligopeptides, cell culture filtrates, DNA fragments, RNA fragments, and water-soluble antioxidants, provides a water-soluble microneedle spicule for scrubs which contains at least one physiologically-active component selected from the above materials, in which the spicule is in the shape of a triangular pyramid or sexangular pyramid in which at least any one among the interior angles of the pyramid base of the spicule is 90 degrees or less.

In order to prepare the non-aqueous cosmetics of the present invention at a lower cost, the present invention provides a non-aqueous cosmetic composition which contains a water-soluble microneedle spicule in the polyangular shape according to the present invention containing at least one of the materials described above and a general water-soluble spicule for scrubs for weight increase or viscosity control in a combined amount of 0.01% wt % to 15% wt %.

The skin cosmetic effective material contained in the water-soluble microneedle spicule of the present invention may be an antioxidant, growth factor, wrinkle improving material, or a cell culture or culture medium.

The antioxidant may be vitamin C or vitamin E, and the growth factor; the growth factor may be an epidermal growth factor (EGF) or fibroblast growth factor (FGF), and the cell culture or culture medium may be a culture product or culture medium of stem cells.

Additionally, the effective material contained in the water-soluble microspicules of the present invention include insulin or growth hormone.

FIG. 11 shows the polyangular pyramid shape of microneedles for absorbing skin cosmetic materials or drugs of the present invention to the skin.

Referring to FIG. 11, the microneedles prepared in the present invention has a polygonal polyangular pyramid structure with at least one tip in which the height of the tip is 1.375 times greater than the width of the polyangular pyramid base. In particular, the tip is a vertex (T) having the longest height among the vertices of the polyhedron. It is preferable that the height (h) of the tip has a length of at least 1.375 times longer than the longest side among the sides forming the base (S).

That is, in the present invention, the aspect ratio (the diagonal length of the base:height from the base to sharp tip) may be 1:1.375 times or greater, preferably 1:1.375 to 10 times, and more preferably 1:1.5 to 5 times.

Alternatively, the microneedles of the present invention may have a ratio of the base (s) to the edge (b) or height (h') of the triangle (M) having the longest height among the faces of the triangle forming the tip may be 1:1.375 or greater.

Additionally, the microneedles of the present invention has an angle of the vertex (θ) of the triangle (M) may be 40 or less, more preferably 30 degrees or less.

The microneedles of the present invention may be a polyangular pyramid, a polyangular pyramid having at least two tips, or a modified angular pyramid or anchor in which the polyangular pyramid and angular columns are bound together.

The microneedles of the present invention are different from the microneedles of Korean Patent Application Publication No. 10-2014-0094471 as follows.

First, the disclosed microneedles are of a tetrahedron or pyramid structure and exhibits almost a regular tetrahedral or quadrangular pyramid structure.

However, the microneedles of the present invention is a shape having a longer distance between the base and the tip. In the case of the conventional microneedle, since the length of the needle tip is small, it is difficult to effectively form micropores in the skin.

However, the microneedles of the present invention can be effectively inserted into the keratin layer because it is a polyangular pyramid having an aspect ratio of 1 to 2 times as described above.

Additionally, in the prior art, polyhedrons such as hexahedron or higher cannot be made into needles, whereas the polyhedral needles of the present invention can effectively form micropores in the skin by providing at least one needle tip even in the case of hexahedral or octahedral structures, as shown in FIG. 11. That is, the microneedles of the present invention shows that polyhedral microneedles having a hexahedron or higher can be prepared.

The objects of the present invention described above can be achieved by providing a non-aqueous cosmetic composition, which contains at least one component among polypeptides, oligopeptides, cell culture filtrates, DNA fragments, RNA fragments, or water-soluble antioxidants, in which a water-soluble microneedle spicule in the shape of a polyangular pyramid of tetrahydron or greater in which at least any one among the interior angles of the pyramid base of the spicule is 90 degrees or less is contained alone or in a mixed content in an amount of 0.01 wt % to 15 wt %.

The water-soluble microneedle spicules of the present invention may contain 0.00001 wt % to 0.1 wt % of a polypeptide or oligopeptide, based on the weight of the particles, and is prepared in the form of shape of a polyangular pyramid of tetrahydron or greater in which at least any one among the interior angles of the pyramid base of the spicule is 90 degrees or less, each containing a polypeptide or oligopeptide having various differences in the structural forms.

The oligopeptide and polypeptide of the present invention is a material in which two to a few hundred thousand amino acids are polymerized by condensation, and the number of amino acids is usually in the range of 2 to a few hundred thousand, preferably in the range of 2 to 1,000, more preferably in the range of 2 to 100, and most preferably in the range of 2 to 80.

The water-soluble microneedle spicules of the present invention containing a polypeptide or oligopeptide can include several types of polypeptide or oligopeptide materials together.

Additionally, the cosmetic composition, which contains a water-soluble microneedle spicules of the present invention in which a polypeptide or oligopeptide is contained, may further contain a water-soluble microneedle spicule which contains a different polypeptide or oligopeptide.

The material used in the present invention may be an oligopeptide growth factor, and in particular, may be epithelial growth factor (EGF).

The water-soluble microneedle spicules of the present invention contains a dried product of a cell culture filtrate in an amount of 0.00001 wt % to 10 wt % based on the weight of the spicules, and is prepared in the form of a water-soluble microneedle spicule with a triangular pyramid or sexangular pyramid in which at least any one among the interior angles of the polyangular pyramid base of the spicule is 90 degrees or less.

In the non-aqueous cosmetic composition of the present invention, at least one water-soluble microneedle spicules with different shapes may be selected and used together. Additionally, the water-soluble microneedle spicule containing a dried product of the cell culture filtrate may further include a polypeptide or oligopeptide.

The cell culture filtrate may be a human stem cell culture filtrate and the polypeptide or oligopeptide may be a growth factor, and in particular, human epidermal growth factor (EGF).

Additionally, the water-soluble microneedle spicules of the present invention may contain 0.00001 wt % to 1 wt % of a DNA fragment or RNA fragment based on its weight, and as particles for scrubs, are prepared in the shape of a triangular pyramid to sexangular pyramid in which at least any one among the interior angles of the polyangular pyramid base of the spicule is 90 degrees or less.

The shape of the microneedle spicules of the present invention is characterized in that the ratio of the diagonal length of the base and the height from the base to the vertex is 1:1 or greater.

In the non-aqueous cosmetic composition of the present invention, at least one kind of the water-soluble microneedle spicules in various shapes having a structural difference from the microneedle spicules of the present invention can be selected, and may be used in combination.

Additionally, the water-soluble microneedle spicule containing a DNA fragment or RNA fragment of the present invention may further contain at least one among polypeptides, oligopeptides, and cell culture filtrates. The cell culture filtrate may be a human stem cell culture filtrate and the polypeptide or oligopeptide may be a growth factor, and in particular, human epidermal growth factor (EGF).

The size of the microneedle spicule of the present invention may be in the range of 0.01 mm to 2 mm. When the size of the microneedle spicule is less than 0.01 mm, the scrubbing effect may be deteriorated, whereas when the size exceeds 2 mm, skin impurities become serious and is thus not desirable. More preferably, the size of the spicule of the present invention is in the range of 0.1 mm to 1 mm.

The shape of the water-soluble microneedle spicule of the present invention is in the shape of a triangular pyramid or sexangular pyramid in which at least any one among the interior angles of the polyangular pyramid base of the spicule is 90 degrees or less, and the length from the base to the tip is longer than the diagonal length of the base, thus being capable of serving the function of a sharp needle.

Alternatively, in the microneedles of the present invention, a depression may be formed on at least one surface, and the depth of the depression may be ½ of the height of the microneedle and those microneedles which are empty inside are also included.

Additionally, the microneedle spicule of the present invention may be in a polyhedral shape in which the aspect ratio is greater than 1, may be provided with tips in one direction or both directions, or has a vertex of a bump structure.

Alternatively, the height of the microneedle spicule of the present invention from the base may be 1 time or greater compared to the diagonal length of the base, preferably in the range of 1.375 to 10 times, and more preferably in the range of 1.5 to 5 times.

The non-aqueous cosmetic composition of the present invention, which contains a water-soluble microneedle spicule of the present invention that contains a polypeptide, oligopeptide, cell culture filtrate, DNA fragment, RNA fragment, or water-soluble antioxidant, may further contain water-soluble particles which are comprised of water-soluble microneedle particles or general cosmetic components not containing an active ingredient, so as to increase weight or control viscosity.

The non-aqueous cosmetic composition of the present invention may be prepared in various forms of cosmetics, such as essence, cream, lotion, etc.

The non-aqueous cosmetic composition of the present invention, which contains a water-soluble microneedle spicule of the present invention that contains a polypeptide, oligopeptide, cell culture filtrate, DNA fragment, RNA fragment, or water-soluble antioxidant, has significant effects of improving skin conditions, such as wrinkle improvement, skin whitening, etc.

The non-aqueous cosmetic composition of the present invention contain a non-aqueous component, which contains 15 wt % to 25 wt % of higher alcohol, 40 wt % to 65 wt % of an oil, 2 wt % to 3 wt % of a wax, and 5 wt % to 20 wt % of tocopheryl acetate. As the higher alcohol, at least one kind may be selected from cetyl alcohol, ceto stearyl alcohol, isostearyl alcohol, and stearyl alcohol, and may be used in combination.

As the oil, at least one kind selected from natural oils such as Jojoba oil, hardened palm oil, avotad oil, olive oil, almond oil, macadamia nut oil, meadow foam oil, palm oil, palm oil, and castor oil may be mixed for use.

Additionally, as the wax, at least one kind selected from synthetic wax and microcrystalline wax may be used and may be used in combination.

The non-aqueous cosmetic composition of the present invention may contain a non-aqueous component which contains the higher alcohol, oil, wax, and tocopheryl acetate, in an amount of 85 wt % to 90 wt %, and preferably 87 wt % to 88 wt %, to facilitate an easier filling into a container by controlling the hardness of cosmetics.

The non-aqueous cosmetic composition of the present invention which contains a water-soluble microneedle spicule in a polyangular shape that contains a polypeptide, oligopeptide, cell culture filtrate, DNA fragment, RNA fragment, or water-soluble antioxidant, may contain 0.5 wt % to 1.9 wt % of hyaluronic acid, 1.5 wt % to 10 wt % of monosaccharide, and 0.00001 wt % to 0.01 wt % of tromethamine. Additionally, a water-soluble microneedle spicule where a polypeptide, oligopeptide, cell culture filtrate, DNA fragment, RNA fragment, or water-soluble antioxidant is not contained, may be included for the purpose of improving the effect of skin penetration or viscosity or hardness control.

The hyaluronic acid used in the water-soluble microneedle spicule in a polyangular shape and the non-aqueous cosmetic composition of the present invention may be selected from sodium hyaluronate and hydrolyzed hyaluronic acid, or a mixture thereof may be used.

The monosaccharide used in the non-aqueous cosmetic composition of the present invention may be at least one kind selected sorbitol and ascorbic acid (vitamin C), and may be used in combination.

The water-soluble microneedle spicules, in which a physiologically-active material is not contained, helps when the non-aqueous cosmetic composition of the present invention is too slippery, or helps the dissolution of the water-soluble microneedle spicules after they are filled into a container.

As the non-aqueous cosmetic composition, a mixture which contains a water-soluble microneedle spicule containing a polypeptide, oligopeptide, cell culture filtrate, DNA fragment, RNA fragment, or water-soluble antioxidant; and a water-soluble microneedle spicule where an active ingredient is not contained, in an amount of 0.01 wt % to 15 wt % is included.

For the preparation of the water-soluble microneedle spicules of the present invention, in which a physiologically-active component such as the polypeptide, oligopeptide, cell culture filtrate, DNA fragment, RNA fragment, or water-soluble antioxidant is contained, and the water-soluble microneedle spicules of the present invention, in which a physiologically-active component such as the polypeptide, oligopeptide, cell culture filtrate, DNA fragment, RNA fragment, or water-soluble antioxidant is not contained, it is preferred to use a low molecular weight hyaluronic acid.

The molecular weight of the hyaluronic acid used in the preparation of the water-soluble microneedle spicules of the present invention is preferably in the range of 0.1 kDa to 50 kDa, and more preferably 0.5 kDa to 10.1 kDa.

Additionally, the non-aqueous cosmetic composition according to the present invention may contain a water-soluble spicule for the increase of weight or viscosity control, and at least one kind of a material selected from monosaccharides, oligosaccharides, polysaccharides, and salts may be further contained.

Preferably, a spicule comprised of hyaluronic acid a monosaccharide may be contained. With regard to the water-soluble spicule for the weight increase of viscosity control of the non-aqueous cosmetic composition of the present invention, it is preferred that those having a size of 2 mm or higher be not used due to impurity problem.

When the non-aqueous cosmetic composition which contains the water-soluble microneedle spicule in a polyangular shape that contains a polypeptide, oligopeptide, cell culture filtrate, DNA fragment, RNA fragment, or water-soluble antioxidant is applied to the skin and rubbed with hands or tapped thereon (see FIG. 12), the area of the vertex or edge of the water-soluble microneedle spicule acts on the skin and removes the keratin layer thereby significantly increasing the skin penetration rate of physiologically-active materials.

Additionally, the water-soluble microneedle spicule contained in the non-aqueous composition of the present invention applied to the skin can be dissolved using the aqueous cosmetic such as water and skin emulsion, and thereby physiologically-active components such as the polypeptide, oligopeptide, cell culture filtrate, DNA fragment, RNA fragment, or water-soluble antioxidant contained in the spicule of polyangular pyramid of the present invention can be uniformly absorbed to the skin thereby providing a skin improving effect.

BEST MODE FOR CARRYING OUT THE INVENTION

Hereinafter, the present invention will be described in more detail with reference to the following Example or drawings. It should be understood, however, that the following examples or drawings are only illustrative of specific embodiments of the present invention, and the scope of the present invention is not intended to be limited or limited to the specific details described herein below.

Example 1: Preparation of Water-Soluble Microneedle Spicules of the Present Invention A glass wafer was coated with a photoresist and the pattern was exposed to light and etched to prepare a mold for positive engraving. The positive mold was plated with nickel and a hot-press was heated to 220° C. to melt the polypropylene and applied with a pressure of 17 kg/cm$^2$ and thereby about 600 positively-engraved polyhedrons were negatively engraved and a negatively-engraved plastic with a size of 6 cm*6 cm was prepared.

A mixed solution (2 g) of hyaluronic acid and water (4 g) was applied to the depressed portion of the negatively-engraved plastic mold. Then, the plastic mold was dried at room temperature and the molded microneedle spicules in the shape of a positively-engraved polyhedron was detached.

When the non-aqueous cosmetic composition of the present invention in which the water-soluble microneedle spicule in the shape of a positively-engraved polyhedron is suspended in a non-aqueous component of the present invention that contains a polypeptide, oligopeptide, cell culture filtrate, DNA fragment, RNA fragment, or water-soluble antioxidant of the present invention is added to general water-containing cosmetics, it can stably maintain the activity of physiologically-active components, such as polypeptides, oligopeptides, cell culture filtrates, DNA fragments, RNA fragments, or water-soluble antioxidants, which are readily hydrolyzed or denatured, at room temperature for the prescribed storage period (see Table 3 and FIG. 17).

Additionally, when the non-aqueous cosmetic composition containing water-soluble microneedle spicules according to the present invention is scrubbed against the skin and the water-soluble microneedle spicules are dissolved using an aqueous cosmetics such as water or a skin emulsion containing high water content, the physiologically-active components contained in the scrub spicules are well penetrated into the skin thereby exhibiting an excellent skin improvement effect (see FIGS. 15 and 16).

FIG. 12 is a conceptual diagram showing the application of the non-aqueous cosmetic composition of the present invention containing water-soluble microneedle spicules in the shape of a polyangular pyramid to the skin.

FIG. 13 is an image under 30-fold magnification showing water-soluble microneedle spicules in the shape of a polyangular pyramid prepared by the present invention.

FIG. 14 is a graph showing the cell proliferation effect of physiologically-active components in which DNA and RNA fragments derived from broccoli, the plant used in the shape of a polyangular pyramid prepared by the present invention.

FIG. 15 is a graph showing statistical comparison results with regard to the effect of changes in skin density of the non-aqueous cosmetic composition of the present invention containing water-soluble microneedle spicules in the shape of a polyangular pyramid, in which human epidermal growth factor (EGF) is contained, upon its application to human body, between the region where the water-soluble microneedle spicule was applied and the region where the water-soluble microneedle spicule was applied after dissolution.

FIG. 16 is a graph showing statistical comparison results with regard to the effect of changes in skin density of the non-aqueous cosmetic composition of the present invention containing water-soluble microneedle spicules in the shape of a polyangular pyramid, in which a dried product of a cell culture filtrate is contained, upon its application to human body, between the region where the water-soluble microneedle spicule was applied and the region where the water-soluble microneedle spicule was applied after dissolution.

FIG. 17 shows the results of a HPLC stability test of the non-aqueous cosmetic composition of the present invention containing water-soluble particles in which vitamin C is contained.

Example 2. Preparation of Water-Soluble Microneedle Spicules Containing Epidermal Growth Factor, Cell Culture Filtrate, DNA Fragment, and RNA Fragment One of the four mixed solutions (i.e., a mixed solution where hyaluronic acid (2 g), water (4 mL), and human epidermal growth factor (EGF) (200 μg) were mixed; a mixed solution where hyaluronic acid (2 g) and a human cell culture filtrate (4 mL) were mixed; a mixed solution where hyaluronic acid (2 g), water (4 mL), and a mixture of DNA and RNA fragments (2 mg), and a mixed solution where hyaluronic acid (2 g), water (3 mL), and vitamin C (1 g) were mixed) was loaded into a plate, where a depressed portion with a negatively-engraving of the shape of the microneedles of the present invention was formed, and dried, and thereby the water-soluble microneedle spicule of the present invention comprised of hyaluronic acid containing physiologically-active materials was prepared (see FIG. 13).

The human cell culture filtrate used in this Example is the cell culture filtrate described in Korean Patent Application Publication No. 10-2010-0098298, and it is a component that contains a plurality of growth factors, has an excellent skin regeneration effect, and approved safety, to be used as a raw material for cosmetics.

Additionally, the DNA and RNA fragments used in this Example is the gene mixture described in Korean Patent Application No. 10-2016-0112143, and it is a physiologically-active component extracted and isolated from a plant which was confirmed with regard to its cell proliferation effect (see FIG. 14) and is a raw material listed in the U.S. Cosmetic Ingredients.

For the human epidermal growth factor, a raw material for cosmetics was purchased and used after confirming its specific biological activity. The vitamin C was used after confirming its activity by HPLC.

Example 3. Preparation of Water-Soluble Spicules for Weight Increase and Viscosity Control A mixed solution where hyaluronic acid and water were mixed in a 1:2 ratio was thinly loaded into a flat plate or tray and pulverized to a size similar to that of water-soluble microneedle spicules of the present invention. Then, water-soluble excipient spicules for weight increase and viscosity control having a size of 2 mm or less were obtained using a mesh or sieve.

The powders of monosaccharides were pulverized to a size similar to that of water-soluble microneedle spicules of the present invention using a pulverizer. The water-soluble excipient spicules for weight increase and viscosity control having a size of 2 mm or less were separated using a mesh.

Examples 4 to 7

According to the compositions shown in Table 1 below, the non-aqueous component, water-soluble microneedle particles containing physiologically-active active ingredients, excipient particles for weight increase and viscosity control, and other components were measured, respectively. Then, in a state heated at 60° C., the mixture was slowly and uniformly mixed in the stirring device for about 5 hours. Then, the mixture was cooled to 30° C. and thereby a non-aqueous cosmetic composition containing the water-soluble microneedle spicules of the present invention was prepared.

Experimental Example 1. Human Patch Test

The safety test on human application of the skin patch application of the non-aqueous cosmetic composition of the present invention containing the water-soluble microneedle spicule of Example 5 was performed. A total of 30 subjects with an average age of 39.5 participated in the test and no subjects dropped out of the test due to adverse reactions.

Formulations containing the water-soluble microneedle spicule were drop-wisely added in an amount of 25 μL to finn chambers, respectively, and placed on the back of each subject and fixed thereon. After 24 hours, the patch was removed and the region was marked with a marking pen, and the skin response was observed 30 minutes, 24 hours, and 48 hours thereafter, and the skin responses were evaluated.

After the patch removal, no irritation was observed at time-points of 30 minutes, 24 hours, and 48 hours, and the average degree of skin response was 0.00. Accordingly, the non-aqueous cosmetic composition of the present invention was determined to have no irritation.

The criteria for skin patch test are as follows.
no irritation: 0.00 to 0.75
slight irritation: 0.76 to 1.50
mild irritation: 1.51 to 2.50
intermediate irritation: 2.51 to 4.00
strong irritation: 4.01 to

TABLE 2

| Evaluation Item | No. of Subjects | After 30 Minutes | After 24 Hours | After 48 Hours | Degree of Skin Response |
|---|---|---|---|---|---|
| Skin Irritability | 30 | — | — | — | 0.00 |

Experimental Example 2. Evaluation of Safety of Active Ingredients

The evaluation was performed on the stability of activity of the human epidermal growth factor (EGF) contained in the water-soluble microneedle spicules, using the non-aqueous cosmetic compositions of the present invention prepared according to the composition of Example 5. For the evaluation of stability, the compositions were filled into opaque plastic syringes and placed at room temperature (25° C.) and

TABLE 1

| Composition (wt %) | | | Example 4 | Example 5 | Example 6 | Example 7 |
|---|---|---|---|---|---|---|
| Non-aqueous Component | Higher Alcohol | Stearyl Alcohol | 12 | 13 | 14 | 13 |
| | | Cetyl Alcohol | 13 | 3 | 1 | 3 |
| | Oil | Jojoba oil | 20 | 0 | 55 | 30 |
| | | Olive Oil | 20 | 55 | 0 | 35 |
| | Wax | Microcrystalline Wax | 2 | 1 | 1 | 1 |
| | | Synthetic Wax | 1 | 1 | 1 | 1 |
| | Tocopheryl Acetate | | 20 | 15 | 15 | 15 |
| Water-soluble Microneedle Spicule Containing Physiologically-Active Active Ingredient | | | 0.1 | 1 | 5 | 10 |
| Water-Soluble Spicule Excipient | Hyaluronic acid | Sodium Hyaluronate | 1 | 1 | 1 | 0.5 |
| | | Hydrolytic Hyaluronic Acid | 0.89 | 0 | 0 | 0 |
| | Monosaccharide | Sorbitol | 9.5 | 0.5 | 4.499 | 1 |
| | | Ascorbic Acid (Vitamin C) | 0.5 | 9.499 | 0.5 | 0.49 |
| | | Tromethamine | 0.01 | 0.001 | 0.001 | 0.01 | high temperature (55° C.) for 3 months, and the activity of EGF in the contents was measured as follows.

The water-soluble microneedle spicule was added to skin emulsions, which are aqueous cosmetics, at the same concentration and amount as in the compositions of Example 5 and used as the control group for the test of activity measurement.

Materials for Experiments

The measurement of the cell proliferation activity on human epidermal growth factor (EGF) was performed using the Balb/c 3T3 fibroblast cell line (ATCC #CCL-163). As the culture medium for subculture of the cell line, DMEM medium containing 10% bovine serum albumin was used and UltraMEM serum-free medium was used as the medium for analysis.

For the standard product for the measurement of EGF activity, the human epidermal growth factor (hEGF:rDNA derived, 91/530, 4000 IU/4 μg/mL) was purchased for use. The measurement of cell proliferation by EGF was performed using the MTS reagent.

Method for Activity Measurement

After 3 months from the point of preparation, the cosmetic compositions of the present invention was weighed and added into UltraMEM serum-free medium, which is the medium for the measurement of activity of epidermal growth factor (calculated from the microneedle spicule content and adjusted to give a final concentration of 1 μg/mL of EGF), vehemently stirred, and the aqueous solution was collected by centrifugation and used for activity analysis.

The extract, for which the activity is to be measured, and a reference product for EGF activity were subjected to a serial 2-fold dilution in a 96-well plate, allowed to be added in an amount of 100 μL per well, and the Balb/c 3T3 fibroblast cells were added at a concentration of $3 \times 10^3$ cells/well, and cultured in an incubator (37° C., 5% $CO_2$) for 72 hours.

Then, 40 μL of the MTS reagent was added to each well, incubated in an incubator (37° C., 5% $CO_2$) for 4 hours, and the absorbance was measured at 490 nm using the microreader, and compared the values between EGF standard and the extract by parallel analysis using the PLA 2.0 program, and the EGF activity per 1 g of the cosmetic composition containing the water-soluble microneedle spicule was calculated considering the extraction recovery rate of 60%.

TABLE 3

| Temperature | Example 4 | Control Group |
|---|---|---|
| Room Temperature (25° C.) | $3.30 \times 10^3$ IU/g | 0 IU/g |
| High Temperature (55° C.) | $2.14 \times 10^3$ IU/g | 0 IU/g |

As shown in Table 3 above, the activity of the epithelial growth factor (EGF) was significantly more stable in a case where the non-aqueous cosmetic composition of Example 5 was added (compared to the test control group). Compared to the average initial EGF activity of the non-aqueous cosmetic composition of Example 5 (i.e., $5.0 \times 10^3$ IU/g), the EGF activity of about 66% was maintained at room temperature and also the EGF activity of about 43% was maintained at high temperature.

Accordingly, it was confirmed that the significantly excellent stable activity of the human epidermal growth factor (EGF) was shown to be exhibited in the non-aqueous cosmetic composition of the present invention.

Example 8. Clinical Tests for Confirming Effect of Non-Aqueous Cosmetic Composition Containing Water-Soluble Microneedle Spicule where Human Epidermal Growth Factor is Contained For 20 healthy men and women without skin disease, clinical tests were performed on the effect of EGF-containing water-soluble microneedle spicules containing human epidermal growth factor (EGF) with regard to the improvement of skin wrinkles, and more exactly, with regard to the improvement on the wrinkles around the eyes.

The control group was applied to the left eye of each subject and the test group was applied to the right eye of each subject. In the control group, the water-soluble microneedle spicule which was dissolved by adding 60% distilled water to the test group was used.

Clinical tests were progressed such that each sample was applied once daily to the skin around the eyes for 4 weeks and the results were observed for 8 weeks.

For the control group, the area for application was cleaned and the control material (0.16 g) was applied for about 40 seconds, whereas for the test group, the area for application was cleaned and the control material (0.1 g) was applied, scrubbed for about 20 seconds, and distilled water (about 60 μL) was added thereto and further scrubbed for about 20 seconds.

Observations and measurements were performed at 1, 2, 4, and 8 weeks after the application of the test material. As a result of the comparison of dermal density with a skin ultrasound equipment, the Ultrascan UC22, around the eye wrinkles on both sides of the eyes of the 20 volunteers, it was confirmed that there was a statistically significant increase at $4^{th}$ week and $8^{th}$ week compared to the control group (see FIG. 15).

Example 9. Clinical Tests for Confirming Effect of Non-Aqueous Cosmetic Composition Containing Water-Soluble Microneedle Spicule where Cell Culture Filtrate Component is Contained For 20 healthy men and women without skin disease, clinical tests were performed with regard to the improvement of skin wrinkles, and more exactly, with regard to the improvement on the wrinkles around the eyes.

The control group was applied to the left eye of each subject and the test group was applied to the right eye of each subject. In the control group, the water-soluble microneedle spicule which was dissolved by adding 60% distilled water to the test group was used.

Clinical tests were progressed such that each sample was applied once daily to the skin around the eyes for 4 weeks and the results were observed for 8 weeks. For the control group, the area for application was cleaned and the control material (0.16 g) was applied for about 40 seconds, whereas for the test group, the area for application was cleaned and the control material (0.1 g) was applied, scrubbed for about 20 seconds, and distilled water (about 60 μL) was added thereto and further scrubbed for about 20 seconds.

Observations and measurements were performed at 1, 2, 4, and 8 weeks after the application of the test material. As a result of the comparison of dermal density with a skin ultrasound equipment, the Ultrascan UC22, around the eye wrinkles on both sides of the eyes of the 20 volunteers, it was confirmed that there was a statistically significant increase at $4^{th}$ week and $8^{th}$ week compared to the control group (see FIG. 16).

Example 10. HPLC Stability Test on Non-Aqueous Cosmetic Composition Containing Water-Soluble Spicule in which Vitamin C is Contained To confirm the stability of vitamin C (ascorbic acid) contained in non-aqueous cosmetics, the content of the reduced form of ascorbic acid was measured by HPLC for 24 months. The non-aqueous cosmetics in an amount of 0.1 g was collected and distilled water was added to a final volume of 1 mL, and vehemently mixed. Then, the water-soluble ascorbic acid was eluted and the aqueous solution containing ascorbic acid was diluted and used for analysis.

The column used was the C18 (4.6×150 mm) and 0.025 M phosphoric acid (pH 2.5) was used for the mobile phase. After adding 10 mM DTT to a 100-fold diluted sample for analysis, the amounts of the reduced form in the sample in which ascorbic acid was all converted to a reduced form and the sample in which 10 mM DTT was not added were compared and thereby the amounts of the ascorbic acid in the reduced form contained in the cosmetics were confirmed.

The samples were prepared for 0, 3, 6, 9, 12, 18, and 24 months and analyzed by HPLC. As shown in FIG. 17, it was confirmed that the amounts of ascorbic acid in the reduced form were continuously maintained for 24 months with a content of 96% or more (see FIG. 17). The amounts of ascorbic acid in the reduced form was calculated as follows.

TABLE 4

| Content of Ascorbic acid = Initial AA/Total AA × 100 |
| --- |
| Initial AA: Original sample without DTT<br>Total AA: Converted sample with DTT |

The invention claimed is:

1. A water-soluble, microneedle spicule of a quadrangular pyramidal shape comprising:
    a vertex having an internal angle of 40 degrees or less;
    a quadrilateral base that is a diamond shape or a parallelogram, wherein two interior angles of the quadrilateral base are less than 90 degrees;
    a height from the quadrilateral base to the vertex that is 1.375 times to 10 times greater than a diagonal length of the quadrilateral base, wherein the height of microneedle spicule is 0.01 mm to 2 mm;
    an empty inside;
    a depression is formed on at least one surface of the microneedle spicule and a depth of the depression is less than ½ of the height of the microneedle spicule; and
    a hyaluronic acid polymer which has a molecular weight of 0.1 kDa to 28 kDa.

2. The water-soluble, microneedle spicule of claim 1, further comprising at least one material selected from the group consisting of polysaccharides, monosaccharides, oligosaccharides, polyvinyl alcohol, carboxyvinyl polymers, cellulose polymers, chitosan, salts, and a mixture thereof.

3. A composition comprising a plurality of particles, each comprising water-soluble, microneedle spicule of claim 1.

4. A method of percutaneous delivery of a material, the method comprising:
    applying, onto skin of a person, a composition comprising the water-soluble, microneedle spicule of claim 1 which contains the material; and
    pressing the composition against the skin.

5. The method of claim 4, wherein the material is selected from the group consisting of polypeptides, oligopeptides, DNA fragments, RNA fragments, antioxidants, insulin, growth hormones, and a mixture thereof.

6. The method of claim 4, wherein the material is selected from the group consisting of human epidermal growth factor (EGF), fibroblast growth factor (FGF), vitamin C, vitamin E, and combinations thereof.

7. A composition, comprising:
    a plurality of micro-spicules; and
    a non-aqueous media mixed with a plurality of micro-spicules,
    wherein at least part of the plurality of micro-spicules comprises the water-soluble, microneedle spicules of claim 1.

8. The composition of claim 7, wherein the micro-spicule comprises a physiologically active material selected from the group consisting of human epidermal growth factor (EGF), fibroblast growth factor (FGF), vitamin C, vitamin E, and combinations thereof.

* * * * *